United States Patent [19]
Mayerl et al.

[11] Patent Number: 5,622,863
[45] Date of Patent: Apr. 22, 1997

[54] **CULTURE OF *EUPENICILLIUM BREFELDIANUM***

[75] Inventors: Friedrich Mayerl, Norwalk; Xiaohua Huang, Wallingford; Qi Gao, Meriden, all of Conn.

[73] Assignee: Bristol-Myers Squibb Co., Princeton, N.J.

[21] Appl. No.: 160,597

[22] Filed: Dec. 1, 1993

Related U.S. Application Data

[62] Division of Ser. No. 956,710, Oct. 5, 1992, Pat. No. 5,284,866.

[51] Int. Cl.$^6$ .................................................. C12N 1/14
[52] U.S. Cl. ............................................. 435/254.1; 514/453
[58] Field of Search ............................. 435/252.2, 254.1; 514/453

[56] References Cited

U.S. PATENT DOCUMENTS

| | | | |
|---|---|---|---|
| 388,843 | 6/1975 | Mizuno et al. | 260/211.5 R |
| 3,896,002 | 7/1975 | Honard et al. | 195/81 |
| 4,656,192 | 4/1987 | Yamato | 514/564 |
| 4,833,079 | 5/1989 | Kamei et al. | 435/148 |
| 4,883,758 | 11/1989 | Kamei et al. | 435/253.5 |

OTHER PUBLICATIONS

Kurobane et al, Tetrahedron Letters, 22:493–496 (1981).
Sunagawa et al, J. Antibiotics, 36(1):25–29 (Jan., 1983)
T. Nozie et al, "Synthesis of Puberulonic Acid", *Faculty of Science, Tohoku University*, v. 33 (1960), pp. 1071–1074.
M. Arakawa CA 62:972 (1965).
S. Matsumoto et al, CA 55:1921, (1960).
Quinn et al, "Quantitative Structure–Activity Relationships of Colchicines against P388 Leukemia in Mice", *J. Med. Chem.*, 24 (1981), pp. 251–256.
Brossi et al, "Biological Effects of Modified Colchicines"., 2. Evaluation of Catecholic Colchines, Colchifolines, Colchicide, and Novel N–Acyl–and N–Aroyldeacetyl-colchicines, *J. Med. Chem.*, 26, (1983). pp. 1365–1369.
Yamato, "Antineoplastic Agent Claimed", 100, 105, 106, Derwent 84–227823/37, (55–9134–720–A), (1984).
Yamoto et al, "Synthesis of Tropoline Derivatives"., *J. Chem. Soc. Perkin Trans.*, (1984), pp. 1301–1304.
Yamoto et al, "Synthesis and Antitumor Activity of Tropolone Derivatives. 3", *J. Med. Chem.*, 29, (1986), pp. 1202–1205.
Weenan et al, "Lucidene, a Bis(benzopyranyl) Sesquiterpene from *Uvaria lucida* ssp. *lucida*", *J. Org. Chem.*, 55, (1990), pp. 5107–5709.
*The Merck Index*, 10th ed. (1983) pp. 352 abd 416.
Tatsuya Arai et al, "Structure of Fusariocin C, A Cytotoxic Metabolite from Fusarium Moniliforme", *Aqric. Biol. Chem.*, 45 (1981), pp. 1689–1692.
Yamato et al, "Synthesis and Antitumor Activity of Tropolone Derivatives. 7.$^1$ Bistropolones Containing Connecting Methylene Chains", *J. Med. Chem.*, 35, (1992), pp. 267–273.
Harris et al, "Isolation and Structure Determination of Pycynidione, A Novel Bistropolone Stromelysin Inhibitor from a *Phoma* sp.", *Tetrahedron.*, 49 (1993), pp. 2139–2144.

*Primary Examiner*—Irene Marx
*Attorney, Agent, or Firm*—Sandra M. Nolan

[57] ABSTRACT

Certain novel 1H-cycloundeca[1,2-b:5,6-b']biscyclohepta(b)pyran analogs are useful as antitumor agents.

1 Claim, No Drawings

CULTURE OF *EUPENICILLIUM BREFELDIANUM*

CROSS-REFERENCE TO RELATED APPLICATION

This is a division of application Ser. No. 07/956,710 filed Oct. 5, 1992, now U.S. Pat. No. 5,284,866.

BACKGROUND

As is well known, antitumor antibiotic agents can be produced via the fermentation of a variety of microorganisms. Antibiotic tropolone compounds were discussed by Nozoe et al in "Synthesis of Puberulonic Acid", *Bull. Chem. Soc. Japan*, 33 (1960) pp. 1071–4.

In 1981 and 1983, researchers reported on the action of colchicine and analogs thereof in treating P388 leukemia in mice. See Quinn et al, "Quantitative Structure—Activity Relationships of Colchicines against P388 Leukemia in Mice", *J. Med. Chem.*, 24 (1981) pp. 251–6 and Brossi et al, "Biological Effects of Modified Colchicines . . . ", *J. Med. Chem.*, 26 (1983) pp. 1365–9.

U.S. Pat. No. 4,656,192 to Yamato discloses alkyl- and hydroxy-substituted tropolones and their use as anti-tumor agents.

Synthesis and antitumor activity of compounds containing two tropolone moieties are described by Yamamoto et al., "Synthesis and antitumor activity of tropolone derivatives . . . ", *J. Med. Chem.*, 35 (1992) pp. 267–273. A natural product containing two tropolone units has been isolated by Sasade et al, "Structure of Fusariocin C . . . . ", *Agric. Biol. Chem.*, 45 (1981) pp. 1689–1692.

THE INVENTION

The invention deals with a new series of chemical compounds. The compounds are 1H-cycloundeca[1,2-b: 5,6-b'] biscyclohepta(b)pyrans and derivatives thereof:

The compounds of the invention conform to structure I:

wherein $R_a$, $R_b$ and $R_c$ are independently selected from H —OP=O(OH)$_2$ or Z and Z is of the formula:

wherein $R^3$ and $R^4$ are independently hydrogen or $C_{1-6}$ alkyl, or $R^3$ and $R^4$ taken together with the carbon atom to which they are attached form $C_{3-6}$ cycloalkylidene;

$R^5$ is —OC(=O)R, —OP=O(OH)$_2$ or —CH$_2$OP=O(OH)$_2$;

$R^6$, $R^7$, $R^8$ and $R^9$ are independently halogen, —OC(=O)R, —OP=O(OH)$_2$ or hydroxy, $C_{1-6}$ alkyl, $C_{1-6}$ alkoxy or hydrogen; but when $R^5$ is —OC(=O)R, one of $R^6$, $R^7$, $R^8$ or $R^9$ must be —OP=O (OH)$_2$;

Q is —(CH$_2$)$_q$—, optionally substituted with one to six same or different $C_{1-6}$ alkyl or $C_{3-6}$ cycloalkyl, or a carbon atom of said —(CH$_2$)$_q$— group can also be part of a $C_{3-6}$ cycloalkylidene group;

and q is 2 to 6;

provided that n is 0 when $R^5$ is —CH$_2$OP=O (OH)$_2$; n is 1 or 0 when $R^5$ is —OC(=O)R or —OP=O(OH)$_2$; and R is $C_{1-3}$ alkyl.

One highly preferred compound has x-ray structure II:

This substituted 1H-cycloundeca[1,2-b: 5,6-b']bis-cyclohepta[b]pyran has been shown to have in vitro cytotoxicity against the HCT-116 tumor cell line.

In addition it showed in vivo antitumor activity against P388 leukemia when administered intraperitoneally. It gave significant increases in the survival times of leukemia-infected mice in a bioassay.

It should be noted that references to "the compound(s)" are intended to include mixtures and all pharmaceutically acceptable derivatives of same. Effective quantities of one or more pharmaceutically acceptable derivatives, preferably salts, of the compounds may be used. By "pharmaceutically acceptable salts" is meant derivatives which are metal or ammonium salts. Suitable metals are alkali metals (e.g., K, Na, Li) and alkaline earth metals (e.g., Mg, Co) and the like.

The new compounds are isolated from culture C39686 and purified by extraction and crystallization as set out herein.

MICROORGANISM DEPOSIT

A biologically pure culture of *Eupenicillium brefeldianum* strain C39686, from which the compounds of the invention can be derived, has been deposited with the American Type Culture Collection (ATCC) in Rockville, Md. It has been added to its permanent collection under Accession code ATCC-74184. The ATCC deposit meets all requirements of the Budapest Treaty and those of 35 USC 112.

The dormant culture is also maintained in the Bristol-Myers Squibb Pharmaceutical Research Institute Culture Collection at 5 Research Parkway, Wallingford, Connecticut 06492.

DESCRIPTION OF THE INVENTION

Unless otherwise stated, all percentages recited are weight percentages, based on total composition weight.

The derivatives conforming to formulas I and II were discovered during a program designed to find novel antitumor compounds from fermentation broths.

These compounds were isolated from a strain C39686 of *Eupenicillium brefeldianum*. They are purified by extraction and crystallization procedures to yield crystalline solids.

FERMENTATION AND TAXONOMY

Compound II is produced by fermentation of a suitable strain of *Eupenicillium brefeldianum*. This *Eupenicillium brefeldianum* strain was isolated from a soil sample collected in Japan. A biologically pure culture of the strain is designated C39686 and is being deposited with the American Type Culture Collection, Rockville, Md., ATCC 74184.

The results of taxonomic studies performed on the strain indicate that the strain is a novel strain of *Eupenicillium brefeldianum*. Colonies on Czapek's Agar attain a diameter of 4.1 cm in 14 days at 28° C. They show a thin basal felt radially furrowed. The center is raised and the surface appears floccose. The center is light yellow with white radiating out. The colony reverse has an orange-yellow center and is colorless towards the margin. Exudate is lacking and no soluble pigments are formed. Conidial structures are very few in number. Cleistothecia occur in a layer adjacent to the agar surface obscured by a layer of vegetative hyphae.

Colonies on malt agar reach a diameter of 4.9 cm in 14 days at 28° C. They are floccose with cleistothecia imbedded under the vegetative hypae. The reverse is pale yellow. No exudate or soluble pigments are formed. Cleistothecia are not hard, measure 150 $\mu$m–200 $\mu$m and are light tan in color. Ripening seems to start in the center of the colony, asci are produced within 7 days and mature in 15 days. By 20 days, the entire colony consists of ascospores.

Asci are born singly on short branches from ascogenous hyphae. They are globose, measure 7 $\mu$m–8 $\mu$m in diameter and contain 8 spores. Ascospores are lenticular in shape and measure 7 $\mu$m–8 $\mu$m in diameter. They are hyaline and finely spinulate with a very faint equatorial furrow.

Conidiophores are smooth-walled and short. Penicilli are monoverticillate with one or two short branches. Phialides measure 7 $\mu$m by 3 $\mu$m. Conidia are smooth and subglobose measuring 3 $\mu$m by 2 $\mu$m. Conidial structure was rarely observed to give a statistically significant number of measurements.

Compound II is prepared by cultivating the proper strain of *Eupencillium brefeldianum*, preferably a strain of *Eupenicillium brefeldianum* having the identifying characteristics of strain C39686 (ATCC 74184) or a mutant or a variant thereof, in a conventional aqueous nutrient medium. The organism is grown in a nutrient medium containing known nutritional sources for fungi, i.e., assimilable sources of carbon and nitrogen plus optional inorganic salts and other known growth factors. Submerged aerobic conditions are preferably employed for the production of large quantities of Compound II, although for production of limited amounts, surface cultures and bottles may also be used. The general procedures used for the cultivation of other fungi are applicable to the present invention.

The nutrient medium should contain an appropriate carbon source, such as glucose and soluble starch. An assimilable nitrogen source, such as fish meat extract, peptone, cottonseed meal, yeast extract or cornsteep liquor should be employed. Nutrient inorganic salts can also be incorporated in the medium so as to provide sodium, potassium, ammonium, calcium, phosphate, sulfate, chloride, bromide, nitrate, carbonate and like ions. Trace elements such as copper, manganese, iron, zinc, etc. are added to the medium if desired, or they may be present as impurities of other constituents of the media.

Production of Compound II can be effected at any temperature conducive to satisfactory growth of the producing organism, e.g., about 18° to about 32° C., and is preferably carried out at temperature of about 28° C. The fermentation may be carried out in flasks or in laboratory or industrial fermentors of various capacity. When tank fermentation is used, it is desirable to produce a vegetative inoculum in a nutrient broth by inoculating a small volume of the culture medium with a slant or a lyophilized culture of the producing organism. After obtaining a viable and active inoculum in this manner, it is transferred aseptically to the fermentation tank charged with production medium for large scale production of Compound II. The medium in which the vegetative inoculum is prepared may be the same as, or different from, that utilized in the tank, as long as good growth of the producing organism is obtained. Further agitation may be provided by a mechanical impeller. Antifoam agents, such as lard oil or silicone oil, may be optionally used.

ISOLATION AND CHARACTERIZATION OF COMPOUND II

The overall isolation process for Compound II is: 2.5 liters of culture broth is extracted with two 1.2 liter volumes of ethyl acetate. The product of the extraction is centrifuged to produce myceli a aqueous and organic portions. The organic portion is then concentrated to dryness and 405 mg. of Extract A (described below) is added. The resultant mix of concentrate and Extract A is dissolved in 40 mL ethyl acetate and refrigerated for several days to yield 44 mg. of Compound II (a slightly yellow crystalline solid).

PREPARATION OF EXTRACT A

Raw fermentation broth (2.5 L) as supplied by Microbiology was thoroughly mixed with 1.2 L of ethyl acetate. The mixture was divided over four centrifuge bottles and centrifuged at 4200 rpm at 5° C. After recovery of the organic phase, a second quantity of 1.2 L ethyl acetate was combined with the mycelium and aqueous phase, mixed and centrifuged. The two ethyl acetate extracts were combined and concentrated on the rotary evaporator to give 405 mg of an amorphous residue.

PREPARATION OF COMPOUND II

The total extract A was dissolved in 40 ml of ethyl acetate and the solution left standing in the refrigerator at 4° C. A crystalline solid formed over several days. After a total of 13 days at 4° C. the supernatant was removed. After drying the solid under high vacuum, the total yield of the compound was 44 mg. Crystals for x-ray studies were prepared by recrystallization from $CHCl_3$/EtOH.

PREPARATION OF COMPOUND II BY TRITURATION OF WHOLE BROTH EXTRACT

Ten liters of whole broth were extracted with 8 liters of ethylacetate. The extract was concentrated to an oil which upon trituration with methanol forms a solid. After washing with cold methanol, 474 mg of compound II are obtained.

PREPARATION OF COMPOUND II BY TRITURATION OF MYCELIAL EXTRACT

The mycelium from ten liters of fermentation broth is recovered and extracted with four liters of ethylacetate. Concentration of the extract to an oil and trituration with methanol gave a solid which was washed with cold methanol. Yield was 106 mg of compound II.

PHYSICO-CHEMICAL PROPERTIES OF COMPOUND II

Description: Slightly yellow, crystalline solid

Molecular Formula: $C_{33}H_{40}O_7$

Molecular Weight: 548

Mass Spectrum/FAB: Kratos MS25

Matrix: Meta Nitro-benzylalcohol m/e 549 (M+H)

Mass Spectrum/High Resolution: m/e 549.2840

Mass Spectrum/EI: Finnigan TSQ70

Major Peaks: m/e 548, 384, 366, 175, 137

Ultraviolet Spectrums: Shimadzu UV2100u Spectrophotometer

Solvent: Methanol

Concentration: 2.2 µg/mL

Absorption Maxima (nm): 256,324(sh) 360 (sh), 366

Infrared Spectrum: Perkin Elmer FTIR Model 1800 Spectrometer

KBr Pellet

Major IR Bands: 3440, 3260, 2950, 2870, 1630, 1595, 1530, 1445, 1425, 1395, 1280, 1178, 1150, 1082, 889 ($cm^{-1}$)

$^1$H-NMR Spectrum: Bruker Model AM-500 Spectrometer

Solvent: $CDCl_3$/DMSO

| Observed Chemical Shifts | | | |
|---|---|---|---|
| ppm | Multiplicity | # of H | J (Hz) |
| 7.02 | s | 1 | |
| 6.97 | s | 1 | |
| 6.89 | s | 1 | |
| 6.84 | s | 1 | |
| 5.63 | d | 1 | 15.9 |
| 5.48 | m | 1 | 15.9, 11.0, 4.0 |
| 4.00 | d | 1 | 11.3 |
| 3.27 | d,d | 1 | 18.4, 13.6 |
| 2.67 | d,d | 1 | 17.3, 4.8 |
| 2.53 | d,d | 1 | 13.3, 4.0 |
| 2.33 | d,d | 1 | 13.3, 11.0 |
| 2.26 | d,d | 1 | 18.4, 3.1 |
| 2.23 | s | 3 | |
| 2.18 | s | 3 | |
| 2.16 | d | 1 | 17.3 |
| 1.95 to 2.05 | m | 2 | 13.8, 13.6, 3.1 |
| 1.55 to 1.65 | m | 2 | 14.1, 4.8, 4.1 |
| 1.33 | d,d | 1 | 13.8, 11.3 |
| 1.22 | s | 3 | |
| 0.94 | s | 3 | |
| 0.91 | s | 3 | |
| 0.87 | s | 3 | |
| 0.56 | d,d | 1 | 14.1, 4.1 |

| C NMR Spectrum: | Bruker Model AM-500 Spectrometer Solvent: $CDCl_3$/DMSO | |
|---|---|---|
| ppm | Multiplicity | Type of Carbon |
| 172.2 | s | Q |
| 170.5 | s | Q |
| 162.6 | s | Q |
| 162.2 | s | Q |
| 160.7 | s | Q |
| 159.7 | s | Q |
| 151.2 | s | Q |
| 150.7 | s | Q |
| 143.7 | d | CH |
| 125.0 | 2 × d | 2 × CH |
| 124.3 | d | CH |
| 123.8 | s | Q |
| 118.7 | s | Q |
| 114.1 | d | CH |
| 112.9 | d | CH |
| 81.5 | s | Q |
| 80.6 | s | Q |
| 69.9 | d | CH |
| 45.9 | t | CH2 |
| 45.6 | t | CH2 |
| 40.9 | d | CH |
| 34.4 | s | Q |
| 33.8 | t | CH2 |
| 32.5 | t | CH2 |
| 31.3 | d | CH |
| 29.6 | t | CH2 |
| 29.1 | q | CH3 |
| 26.6 | 2 × q | 2 × CH3 |
| 26.6 | q | CH3 |
| 18.8 | q | CH3 |
| 15.5 | q | CH3 |

ADMINISTRATION

The compounds may be administered to a host, preferably a human being, in antitumor effective quantities, via a variety of routes. Thus, topical, oral, intraperitoneal or intramuscular injection, buccal, ocular, suppository or other forms can be used. Intraperitoneal injection is a preferred route of administration.

EXAMPLES

The present invention is illustrated by the following examples which are not intended to be construed as limiting the scope of the invention.

Example 1. Preparation of frozen vegatative inoculum of the *Eupenicillium brefeldianum* strain C39686.

*Eupenicillium brefeldianum*—containing culture C39686 was maintained as a cryopreserved culture at −80° C. in a Revco ultralow temperature freezer. To prepare a cryopreserved culture, strain C39686 was grown in test tubes on slants of Sabourand Dextrose agar (Difco) with the following composition:

| | |
|---|---|
| Neopeptone | 10.0 g |
| Bacto dextrose | 40.0 g |
| Bacto agar | 15.0 g |
| Deionized water | q.s. to 1 liter |

The agar slant was incubated at 28° C. for 7–10 days. Vegetative culture was prepared by transferring the surface growth aseptically from the slant culture to a 500 ml Erlenmeyer flask containing 100 ml of a sterile vegetative medium consisting of:

| | |
|---|---|
| Soluble Starch | 5.0 g |
| Glucose | 5.0 g |
| Fishmeat Extract | 1.0 g |
| Yeast Extract | 1.0 g |
| NZ-case | 2.0 g |
| Sodium Chloride | 2.0 g |
| Calcium Carbonate | 1.0 g |
| Deionized Water | q.s to 1 liter |

The vegetative culture was incubated at 28° C. for 72 hours on a rotary shaker set at 250 rev/min. The vegetative culture was mixed with equal volume of cryoprotective solution consisting of:

| | |
|---|---|
| Sucrose | 100 g |
| Glycerol | 200 g |
| Deionized water | q.s. to 1 liter |

Four ml portions of this mixture were transferred to sterile cryogenic tubes (5 ml capacity, Corning) and were frozen in a dry ice-acetone bath. The frozen vegetative cultures were then stored at −80° C. in a Revco ultralow temperature freezer.

Example 2. Preparation of vegetative culture of the *Eupenicillium brefeldianum* strain C39686.

Vegetative culture was prepared by transferring 4 ml of the cryopreserved culture to a 500 ml Erlenmeyer flask containing 100 ml of a sterile vegetative medium having the same composition as the cryopreserved vegetative culture. The strain was incubated at 28° C. for 72 hours on a rotary shaker set at 250 rev/min.

Example 3. Fermentation in shake flask culture.

Four ml of the vegetative culture of Example 2 was inoculated into 500 ml Erlenmeyer flasks each containing 100 ml of a production medium consisting of:

| | |
|---|---|
| Soluble Starch | 20.0 g |
| Bacto Peptone | 5.0 g |
| Yeast Extract | 5.0 g |
| Cerelose | 10.0 g |
| Calcium Carbonate | 1.0 g |
| Deionized Water | q.s. to 1 liter |

The production culture was incubated at 28° C. on a rotary shaker set at 250 rev/min for 5 days. Maximum production of compound II was obtained at about 5 days according to the cytotoxicity assay.

The following examples illustrate the anti-tumor activity of the compounds of the invention.

Example 4.

Determination of in vitro cytotoxicity in tissue culture cells.

Cytotoxicity was assessed in HCT-116 and HCT-VM46 human colon carcinoma cells by XTT (2,3-bis(2-methoxy-4-nitro-5-sulfophenyl)-5-[(phenylamino)carbonyl]-2H-tetrazolium hydroxide assay. See Scudiero, DA, Shoemaker, RH, Paull, KD, Monks, A, Tierney, S, Nofziger, TH, Currens, MJ, Seniff, D, and Boyd, MR., "Evaluation of a soluble tetrazolium/formazan assay for cell growth and drug sensitivity in culture using human and other tumor cell lines", *Cancer Res.* 48: 4827–4833 (1988). Cells were plated at 4000 cells/well in 96 well microtiter plates and 24 hrs later drugs were added and serially diluted. The cells were incubated at 37° C. for 72 hrs at which time the tetrazolium dye, XTT, was added. A dehydrogenase enzyme in live cells reduces the XTT to a form that absorbs light at 450 nm which can be quantitated spectrophotometrically. The greater the absorbance the greater the number of live cells. The results are expressed as an $IC_{50}$ which is the drug concentration required to inhibit cell proliferation (i.e., absorbance at 450 nm) to 50% of that of untreated control cells.

Compound II has an IC (μg/mL) of 0.005 on HCT-116 cells and 0.002 on HCT-VM46 cells.

Example 5.

The in vivo activity of compound II against P388 leukemia in mice was studied using the following procedure:

Compound II was given intraperitoneally beginning one day post leukemia implant ($10^6$ cells IP) and once daily for five consecutive days.

In Vivo Activity of Compound II in Treating P388 Leukemia in Mice.

| Dose (mg/kg/day) | Median Survival Time | % T/C | Body Weight Change on Day 4 |
|---|---|---|---|
| 2 | 9.0 | 82 | −3.0 |
| 1 | 15.0 | 136 | −3.5 |
| 0.3 | 13.5 | 123 | −1.6 |
| control | 11.0 | 100 | −0.7 |

Reasonable variations, such as those which would occur to a skilled artisan, can be made herein without departing from the scope of the invention.

We claim:

1. A biologically pure culture of *Eupenicillium brefeldianum* strain C39686, ATCC-74184, which produces the compound of Structure II in a recoverable amount in an aqueous nutrient medium containing assimilable sources of carbon, nitrogen and inorganic substances, wherein Structure II is:

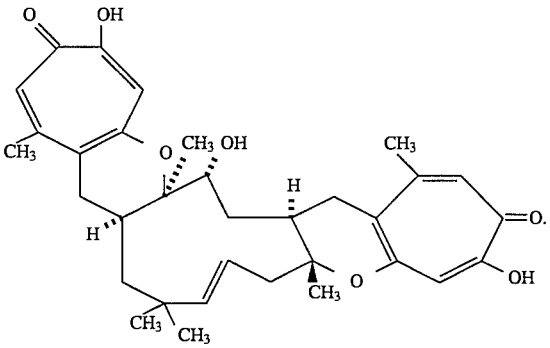

(II)

* * * * *